(12) United States Patent
Ryan

(10) Patent No.: US 6,454,045 B1
(45) Date of Patent: Sep. 24, 2002

(54) STETHOSCOPE WITH OPTICAL FIBER LIGHT

(76) Inventor: Eileen Marie Ryan, 11 Washington Cir., Suffern, NY (US) 10901

( * ) Notice: Subject to any disclaimer, the term of this patent is extended or adjusted under 35 U.S.C. 154(b) by 0 days.

(21) Appl. No.: 09/656,246

(22) Filed: Sep. 6, 2000

(51) Int. Cl.[7] .................................................. A61B 7/02
(52) U.S. Cl. ........................ 181/131; 381/67; 600/528
(58) Field of Search ........................... 181/131; 381/67; 600/528; D24/134

(56) References Cited

U.S. PATENT DOCUMENTS

| | | | | |
|---|---|---|---|---|
| 2,566,687 A | * | 9/1951 | Wehby | 181/131 |
| 4,254,302 A | * | 3/1981 | Walshe | 381/67 |
| 5,029,591 A | * | 7/1991 | Teves | 600/528 |
| 5,514,840 A | * | 5/1996 | Selinger | 181/131 |
| 5,616,890 A | * | 4/1997 | Boussignac | 181/131 |
| 5,825,895 A | * | 10/1998 | Grasfield et al. | 381/67 |
| 5,989,186 A | * | 11/1999 | Alatriste | 181/131 |
| 6,202,784 B1 | * | 3/2001 | Alatriste | 181/131 |

* cited by examiner

*Primary Examiner*—Bentsu Ro
*Assistant Examiner*—Edgardo San Martin
(74) *Attorney, Agent, or Firm*—Brian L. Wamsley

(57) ABSTRACT

A stethoscope having an optical fiber light for providing light suitable for patient examination emanating from the chestpiece of the stethoscope. A battery operated light source is provided near the junction of the binaurals and light is transmitted by optical fiber along the stethoscope tubing into the chestpiece and out the side opposite the tubing. A switch for activating and deactivating the light can be operated by manipulation of the binaurals or rotation of the chestpiece.

20 Claims, 4 Drawing Sheets

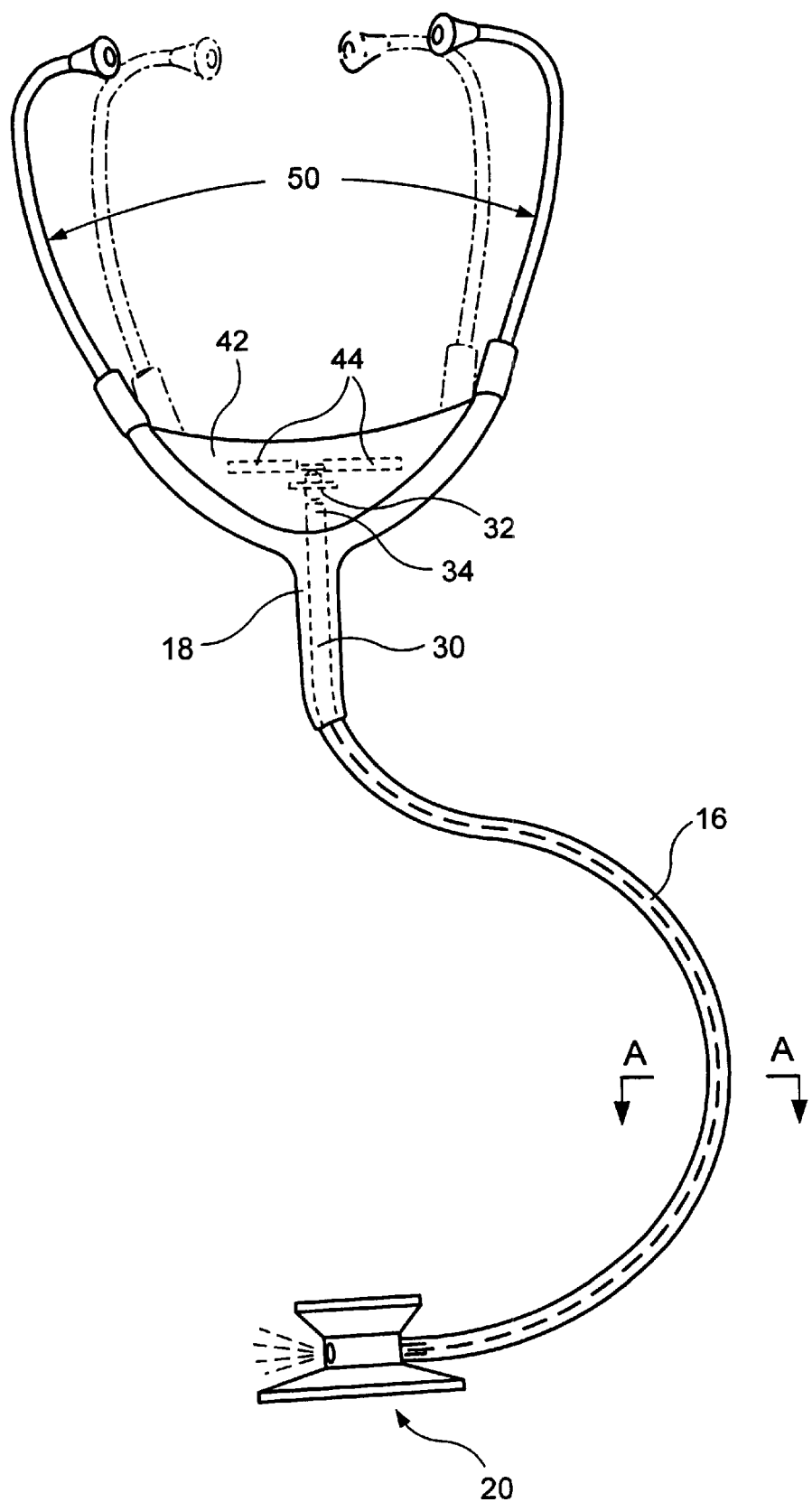
F I G. 2

STETHOSCOPE WITH OPTICAL FIBER LIGHT

BACKGROUND OF THE INVENTION

The present invention relates to a stethoscope having a light suitable for patient examination. More particularly, the invention relates to a stethoscope providing a narrow beam, optical fiber light where the optical fiber emits light from the stethoscope chestpiece. The source of the light transmitted through the optical fiber is located at the junction of the stethoscope binaurals, where the binaurals connect to the stethoscope tubing. The optical fiber extends from the light source along the length of the tubing into the chestpiece, emitting a beam of light emitted from the opposite side of the chestpiece. In this manner a medical practitioner always has a convenient source of light within arm's reach suitable for patient examination.

A small but focused beam of light is frequently used by medical practitioners for examining patients' eyes, ears, nose and throat, among other uses. For example, physicians and nurses use light beams to examine patients' eyes, to chart pupillary size and response to light, as well as to inspect portions and alignment of the eyes and characteristics of the external eye structure. Otoscopes with lights are used to examine the condition of the ear canal and eardrum, and to safely visualize the presence of foreign objects. With regard to the nose and sinus, light is useful in determining source or nature of sinus drainage, or detect nasal obstruction that may interfere with breathing. Lights also can illuminate the supraorbital ridge or frontal bone and illuminate frontal and maxillary sinuses.

Normally, medical practitioners use small, individual flashlights to provide light sources, particularly for examining eyes, nose and throat. These flashlights are specifically designed for this purpose and are typically carried in the practitioner's shirt pocket. However, they are often set down, misplaced or borrowed by other practitioners, particularly in busy hospital or clinic examining areas shared by many practitioners. Thus, practitioners are frequently faced with the situation of being without an examining light and having to search for one. It would therefore be desirable for a practitioner to have a light source that is readily available and convenient, easy to use, that is not easily misplaced or likely to be borrowed.

Accordingly, it would be desirable to have a light source in combination with a stethoscope. Medical practitioners that would use an examining light source also use stethoscopes as an indispensable instrument. Generally worn about the neck, even when not in use, practitioners tend to guard their stethoscopes and not lend them to other practitioners. Because of their indispensability and frequent use, stethoscopes are kept readily at hand and are seldom, if ever, set down so that they can become misplaced. By having a light emanating from the chestpiece of the stethoscope, a light is available at arm's reach, providing convenience and ease of use.

It is also desirable to use a light beam of the type transmitted through optical fibers. An optical fiber produces a cool, focused light beam with no reflections or obstruction. Further, halogen light sources can be used which provide more light output than incandescent lights, resulting in truer tissue color and consistent, long-lasting illumination.

It is therefore an object of this invention to provide an examination light that is convenient, easy to use and readily available, and that is not easily lost or misplaced, nor likely to be borrowed. It is also an object of this invention to provide a stethoscope which also functions to provide a convenient source of an examination light. It is a further object of this invention to provide an optical fiber light suitable for patient examination.

SUMMARY OF THE INVENTION

In accordance with a preferred embodiment of the present invention, there is provided a stethoscope having a light emanating from its chestpiece. The stethoscope generally comprises a pair of binaurals connected at a junction to tubing which leads to the chestpiece. The chestpiece comprises a circular metallic device having a conical bell on one side and a diaphragm on the other, separated by a cylindrical chestpiece member. An electrical light source is located preferably at the binaural junction, which illuminates one end of an optical fiber. The light source comprises a light bulb, a source of power such as a battery, and means for activating or deactivating the bulb. The optical fiber extends from the light source along the length of the tubing to the chestpiece. It is positioned on the outside of the stethoscope tubing so as not to cause interference with the acoustical properties of the tubing itself. A covering or sheath can be placed over the tubing and the optical fiber to hold the optical fiber in place. The optical fiber light of this invention may be used with both single tube stethoscopes and double tube Sprague stethoscopes.

After reaching the chestpiece, the optical fiber passes into the chestpiece in the central piece between the bell and the diaphragm. In the preferred embodiment, the optical fiber passes directly through the chestpiece, in a manner so as not to interfere with the acoustical properties of the chestpiece, and terminates on the opposite side in an opening or channel for the beam of light to exit. However, the optical fiber may also be configured to emit light at any other suitable position on the chestpiece, such as the edge of the diaphragm. Having the light emitted from the chestpiece itself affords the user a very convenient means for holding and using the light. As stethoscopes are generally worn around the practitioner's neck by the binaurals, even when not in active use, the chestpiece/light is always handy and within arm's reach.

For added convenience, the chestpiece may further comprise means for activating and deactivating the bulb at the binaural junction. Such means include toggle or slide switches, push button switches, push and hold switches and "twist" switches.

BRIEF DESCRIPTION OF THE DRAWINGS

The above objects and advantages of the invention will become manifest to one skilled in the art from considering the following detailed description of an embodiment of the invention in light of the accompanying drawings, in which:

FIG. 2 is a further view of the stethoscope with optical fiber light of FIG. 1, showing one manner or activating or deactivating the light source;

DETAILED DESCRIPTION OF THE INVENTION

Figure 1:
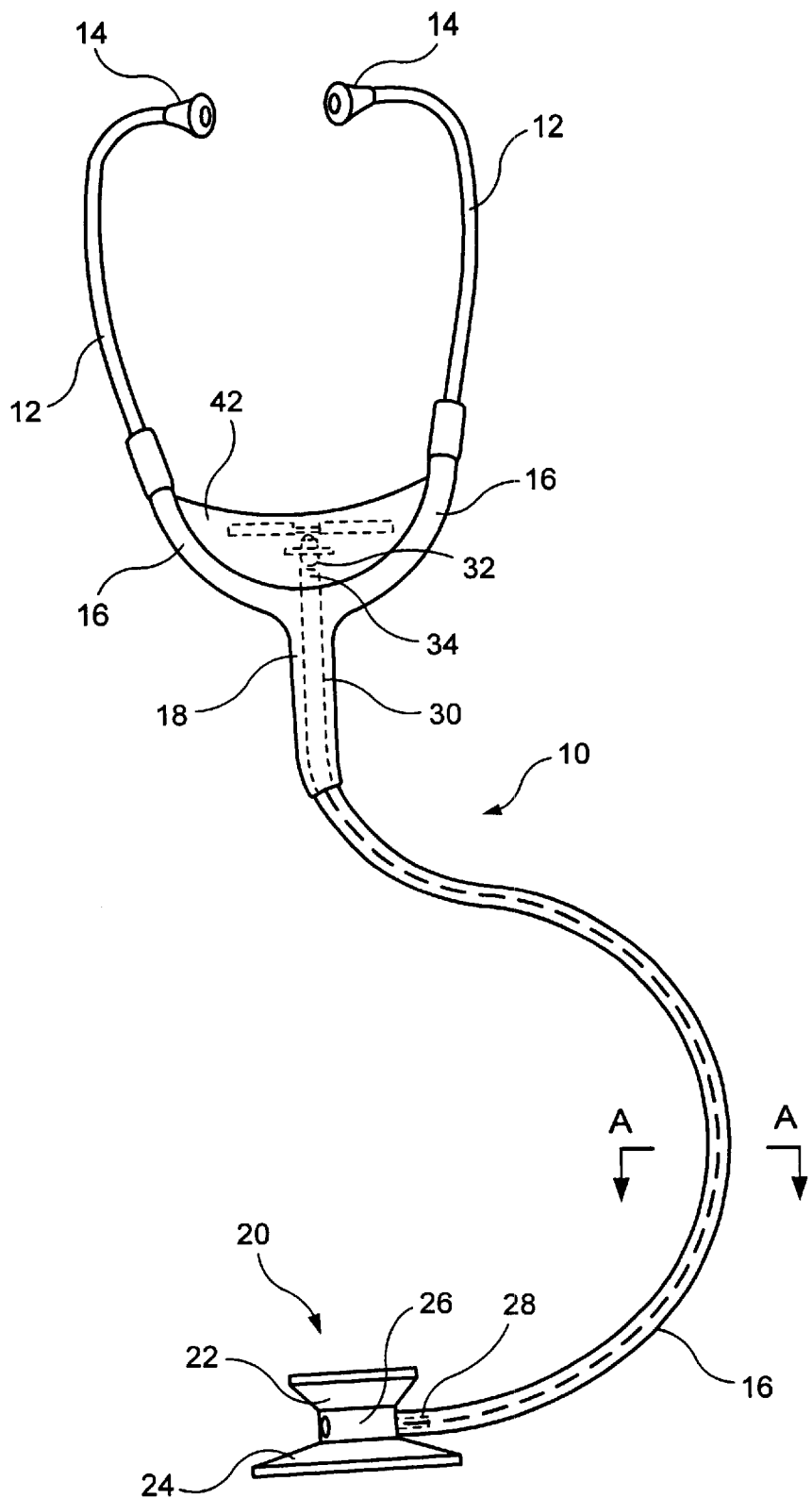
FIG. 1 is a of the stethoscope with optical fiber light of the present invention.
Figure 3:
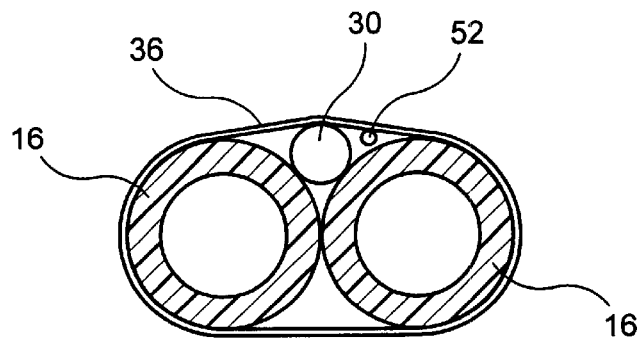
FIG. 3 is a cross-sectional view of the stethoscope tubing along A—A, for a Sprague stethoscope.

Referring now to the drawings wherein the showings are for the purpose of illustrating a preferred embodiment of the present invention and not for purposes of limiting the same, FIGS. 1 and 2 perspectively illustrate the stethoscope with optical fiber light 10 of the present invention. The stethoscope generally comprises a pair of binaurals 12, usually made of metal such as steel, ending in ear pieces 14 for acoustical connection of the stethoscope 10 with the ears of the user. Latex tubing 16 is attached at the end of the binaurals 12 opposite the ear pieces, and merges at junction 18 to form a single tube with terminates at chestpiece 20. Chestpiece 20 is comprised of a bell 22 and a diaphragm 24 separated by a cylindrical frame member 26 which has a stem 28 for attachment of tubing 16. In many stethoscopes, bell 22 and diaphragm 24 freely rotate axially with respect to frame member 26.

Referring now to FIGS. 1–4, in accordance with this invention an optical fiber 30 extends from above tubing junction 18 along the tubing 16 and terminates within chestpiece 20. A source of light 32, primarily a light bulb as designed to provide sufficient light to optical fiber 30, is positioned adjacent the proximal end 34 of optical fiber 30. It is preferred, however, that halogen lamps such as the 3.5 volt halogen lamp currently known in the art be used as the light source. Halogen lamps produce about 30% more light than incandescent bulbs, resulting in superior illumination. The optical fiber 30 can be any type of optical fiber for transporting light adequate for the purpose of this invention, that my be known to those of skill in the art. Further, the thickness or diameter of optical fiber 30 can be of varying degree as necessary, but generally optical fibers having diameters in the range of 1 mm to 5 mm can be used, with diameters of about 3–4 mm being preferred.

Figure 4:
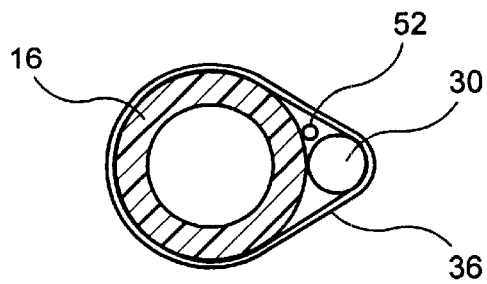
FIG. 4 is a cross-sectional view of the stethoscope tubing along A—A, for a single tube stethoscope.
Figure 7:
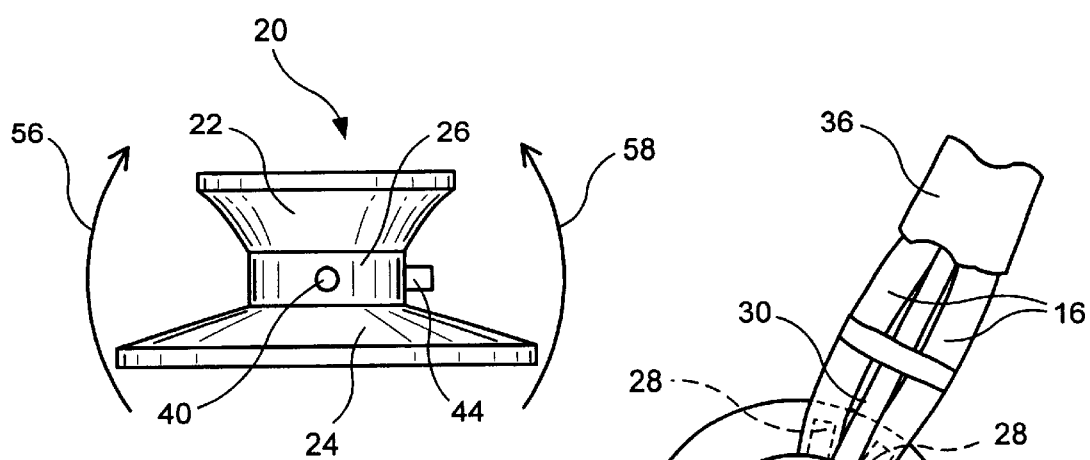
FIG. 7 is an end view of the chestpiece.

In the preferred embodiment of this invention, the optical fiber 30 is disposed adjacent to the acoustical tubing 16, so as not to interfere with the acoustical properties of tubing 16. FIG. 4. However, it is contemplated that the optical fiber 30 may be placed inside the tubing 16, or even embedded within the tubing wall itself (not shown). It is also preferred that the tubing 16 together with optical fiber 30 be wrapped in a covering means such as a sheath 36, which could be fabric, rubber or any other suitable material. Besides offering protection and support to the optical fiber 16, the sheath 36 securely holds the fiber 30 against the tubing 16 to reduce extraneous noise caused by the friction of the fiber 30 rubbing against the tube(s) 16. When the optical fiber light is used with the double tube Sprague stethoscope, the optical fiber 30 is placed between tubes 16. See FIG. 3. Sheath 36 can also secure a thin electrical wire 52 which is necessary for certain embodiments where the switching means is provided in the chestpiece 20. See FIG. 7.

Figure 5:
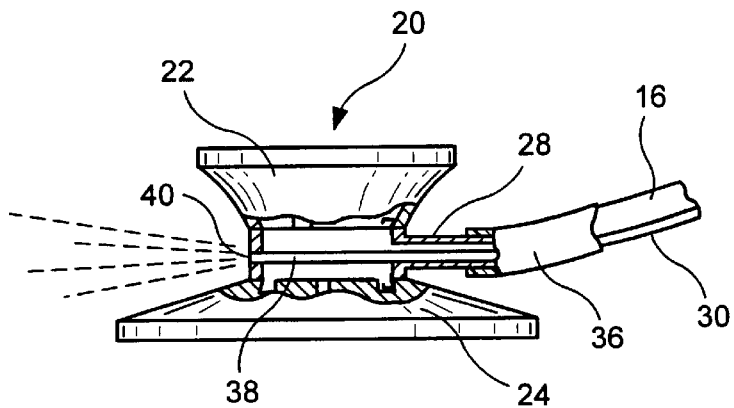
FIG. 5 is a cross-sectional view of the chestpiece of the invention.
Figure 6:
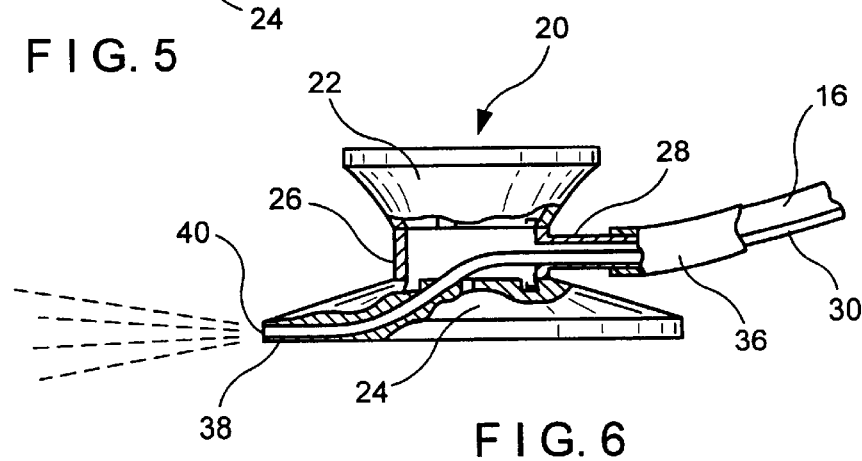
FIG. 6 is the cross-sectional view of a further embodiment of the chestpiece.

Referring now to FIGS. 5 and 6, the tubing 16 ends at the chestpiece 20, usually by connection to the stem 28 which protrudes from cylindrical frame member 26. The distal end 38 of the optical fiber 30, however, enters the chestpiece 20 through the stem 28 and continues through the chestpiece 20 and terminates at an opening 40 located in chestpiece 20 opposite the stem 28. Opening 40 permits a beam of light to be emitted from optical fiber 30, and can be positioned at any suitable location on the chestpiece 20. FIG. 5 illustrates optical fiber 30 passing directly through the frame member 26 of the chestpiece 20, ending 180° opposite stem 28. FIG. 6 on the other hand, illustrates the distal end 38 ending along the rim of diaphragm 24, again at 180° opposite stem 28. Although either of these locations for the distal end 38 allow the user ready and convenient access to a light beam by manually holding the chestpiece 20, other locations may also be used.

Figure 8:
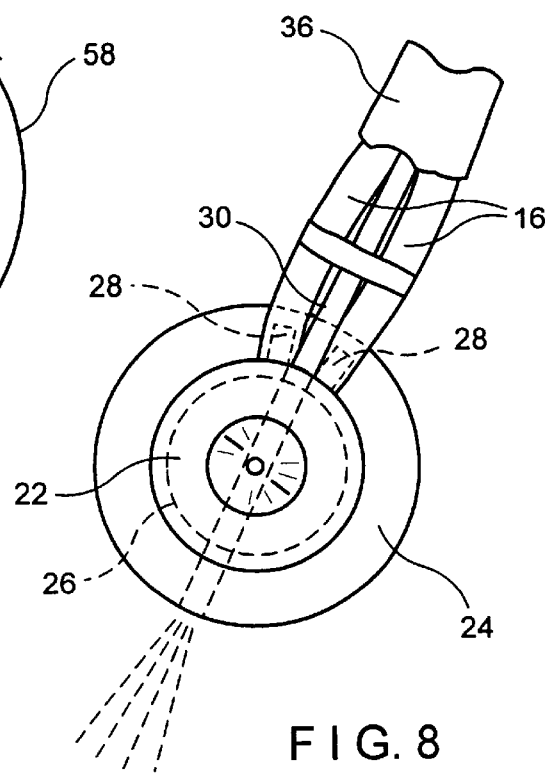
FIG. 8 is a top view of the chestpiece of a Sprague stethoscope.

In the Sprague stethoscope embodiment, FIG. 8, two stems 28 protrude from cylindrical frame member 26 for attachment of the latex tubes 16. While it is a design choice, optical fiber 30 may directly enter frame member 26 as shown, or may enter through one of the stems 28 as in FIG. 6. In either case, the terminal end of the optical fiber would be the same as in the single tube stethoscope.

Figure 9:
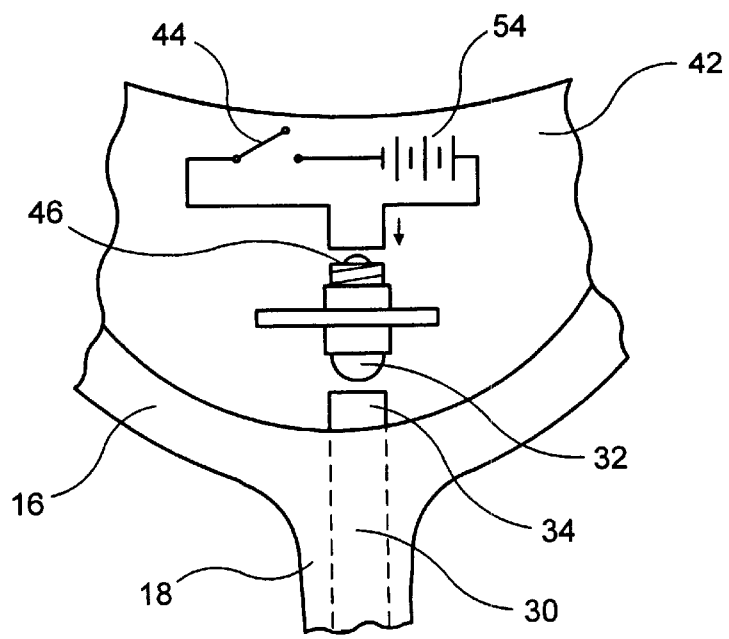
FIG. 9 is a view of the proximal end of the optical fiber at the binaural junction.

Referring to FIGS. 1, 2 and 9, a compartment 42 is provided between the binaurals 12 at the junction 18 of the tubes 16 and adjacent the proximal end 34 of optical fiber 30. Compartment 42 houses the light source 32 and the electrical components necessary for operation of the light source 32. Typically a light bulb of the type suitable for providing light to be transmitted through an optical fiber, the light source 32 is positioned adjacent the proximal end 34 of optical fiber 30. It is preferred that a 3.5v halogen lamp of the type known in the art is utilized as the light source. Light source 32 is powered by battery means 54 contained in compartment 42. A number of types of batteries to provide sufficient voltage to illuminate the light can be used, such as standard "C" dry cell batteries, but rechargeable lithium-ion batteries or nickel-cadmium are preferred. The size of the battery determines the amount of time the light can be operated.

Switching means 44 for activating and deactivating the light is also housed in compartment 42. The switching means 44 can be of any suitable type known to those of skill in the art, such as a push button, toggle switch or the like. In one embodiment of the invention, the switching means 44 comprises a pull-switch which may close a contact 46 with light source 32, completing an electrical circuit, when the binaurals 12 are manually pulled apart in direction 50 (FIGS. 2 and 9). This pull-switch can be of the type used on a common lamp, a ratchet type device activated by pulling a chain, for example. Thus, when binaurals 12 are pulled apart to activate light source 32, they may be relaxed to be pulled apart a second time to deactivate the light source.

In other embodiments of the invention, the switching means 44 is located in chestpiece 20. The switch could be an on/off push button or toggle switch, but it is preferred that switching means 44 be a push and hold switch, which activates the light 32 as long as the button is held down, and deactivates the light when the button is released. Alternately, the chestpiece itself could become the switch. In this embodiment, the entire chestpiece 20 is be rotated in a clockwise direction 56, for example, on an axis in line with stem 28, to activate light source 32. This operation is much the same mechanism commonly employed in certain flashlights, where the lenspiece is rotated against the flashlight body. Similarly, rotating the chestpiece 20 in the opposite or counterclockwise direction 58 would deactivate the light source 32. See FIG. 7. In both these embodiments, a thin electrical wire 52 must be used to connect the switching means 44 of the chestpiece 20 with the power source in compartment 42. Thus, electrical wire 52 may be contained in sheath 36 as it extends from the chestpiece 20 to the binaural junction 18.

Additional modifications and improvements of the present invention may also be apparent to those skilled in the art. Thus, the particular combination of parts described and illustrated herein is intended to represent only one embodiment of the invention, and is not intended to serve as limitations of alternative devices within the spirit and scope of the invention.

What is claimed is:

1. A stethoscope having an optical fiber light, comprising;
   a pair of binaurals for inserting into the user's ears;
   acoustical tubing connected to the binaurals at a junction;
   a chestpiece attached to an end of the acoustical tubing opposite the binaurals, said chestpiece being capable of receiving internal sounds from a patient;
   an optical fiber for transmitting light positioned adjacent the acoustical tubing and extending along said tubing from about the tubing junction to the interior of the chestpiece, wherein a distal end of the optical fiber extends through the chestpiece and terminates at an opening in said chestpiece;
   a source of light at a proximal end of the optical fiber, wherein light from the light source is transmitted through the optical fiber to exit the optical fiber at the distal end, providing a beam of light suitable for medical examination purposes.

2. The stethoscope of claim 1, further comprising electrical supply means for operating the light source.

3. The stethoscope of claim 2, wherein the electrical supply means comprises one or more dry cell batteries.

4. The stethoscope of claim 1, further comprising switching means for activating and deactivating the light source.

5. The stethoscope of claim 1, further comprising covering means for wrapping the optical fiber together with the acoustical tubing.

6. The stethoscope of claim 1, wherein the acoustical tubing comprises a pair of acoustical tubes adjacent each other.

7. The stethoscope of claim 1, further comprising switching means located in the chestpiece for activating and deactivating the light source.

8. The stethoscope of claim 1 wherein the switching means is activated and deactivated by pulling apart the binaurals away from each other.

9. The stethoscope of claim 7, wherein the switching means located in the chestpiece is a button that is pushed and held to activate the light, and released to deactivate the light.

10. The stethoscope of claim 7, wherein the switching means located in the chestpiece comprises means for activating and deactivating the light source by axially rotating the chestpiece.

11. A stethoscope having an optical fiber light, comprising;
    a pair of binaurals;
    acoustical tubing connected to the binaurals at a junction;
    a chestpiece attached to an end of the acoustical tubing opposite the binaurals, said chestpiece being capable of receiving internal sounds from a patient;
    an optical fiber for transmitting light extending from about the tubing junction to the interior of the chestpiece, wherein a distal end of the optical fiber extends through the chestpiece and terminates at an opening in said chestpiece;
    a source of light at a proximal end of the optical fiber, wherein light from the source is transmitted through the optical fiber to exit the optical fiber at the distal end, providing a beam of light suitable for medical examination purposes.

12. The stethoscope of claim 11, further comprising electrical supply means for operating the light source.

13. The stethoscope of claim 11, wherein the electrical supply means comprises one or more dry cell batteries.

14. The stethoscope of claim 11, further comprising switching means for activating and deactivating the light source.

15. The stethoscope of claim 11, further comprising covering means for wrapping the optical fiber together with the acoustical tubing.

16. The stethoscope of claim 11, wherein the acoustical tubing comprises a pair of acoustical tubes adjacent each other.

17. The stethoscope of claim 11, further comprising switching means located in the chestpiece for activating and deactivating the light source.

18. The stethoscope of claim 17, further comprising electrical conductor means connecting the switching means in the chestpiece with the electrical supply for operating the light source.

19. The stethoscope of claim 11, wherein the switching means is activated and deactivated by pulling apart the binaurals away from each other.

20. The stethoscope of claim 17, wherein the switching means located in the chestpiece is a button that is pushed and held to activate the light, and released to deactivate the light.

* * * * *